US00PP17987P3

(12) United States Plant Patent
Jandrew

(10) Patent No.: US PP17,987 P3
(45) Date of Patent: Sep. 4, 2007

(54) ***PENSTEMON* PLANT NAMED 'PHENI MAGNA'**

(50) Latin Name: ***Penstemon hartwegii* Benth**
Varietal Denomination: Pheni Magna

(75) Inventor: Jason Jandrew, Gilroy, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 15 days.

(21) Appl. No.: 11/302,443

(22) Filed: Dec. 13, 2005

(65) Prior Publication Data

US 2007/0136915 P1 Jun. 14, 2007

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
*Assistant Examiner*—Georgia Helmer

(74) *Attorney, Agent, or Firm*—Jondle & Associates P.C.

(57) ABSTRACT

A new *Penstemon* plant particularly distinguished by large red-purple flowers with white throats, large inflorescences, early flowering, medium to grass-green foliage with lanceolate leaves, vigorous growth, and an upright, robust and relatively compact plant habit with steady stems is disclosed.

2 Drawing Sheets

Genus and species: *Penstemon hartwegii* Benth.
Variety denomination: 'Pheni Magna'.

BACKGROUND OF THE NEW PLANT

The present invention comprises a new and distinct cultivar of *Penstemon,* botanically known as *Penstemon hartweggi,* and hereinafter referred to by the cultivar name 'Pheni Magna'. The new cultivar originated from a hybridization made in 2002 in Gilroy, Calif. The female parent is a proprietary *Penstemon* plant designated '110-1' (unpatented), having red flowers and the male parent is a proprietary *Penstemon* plant designated '112-1' (unpatented), having lavender flowers. The seeds produced by the hybridization were sown in November 2002, and the resulting seedlings were selected in May 2003. A single plant selection was chosen for further evaluation and for asexual propagation in the summer of 2003.

The new cultivar was created in 2002 in Gilroy, Calif. and has been asexually reproduced repeatedly by vegetative cuttings and tissue culture in Gilroy, Calif. over a three-year period. The plant has also been trialed at Gilroy, Calif., and Hillscheid, Germany. The present invention has been found to retain its distinctive characteristics through successive asexual propagations.

Plant Breeder's Rights for this cultivar were applied for in Europe on Oct. 14, 2005 and in Canada on Mar. 29, 2005.

SUMMARY OF THE INVENTION

The following are the most outstanding and distinguishing characteristics of this new cultivar when grown under normal horticultural practices in Gilroy, Calif. and Hillscheid, Germany.

1. Large red-purple flowers with white throats;
2. Large inflorescences;

3. Early flowering;
4. Medium to grass-green foliage with lanceolate leaves;
5. Vigorous growth; and
6. An upright, robust and relatively compact and steady plant habit with steady stems.

DESCRIPTION OF PHOTOGRAPHS

This new *Penstemon* plant is illustrated by the accompanying photographs which show blooms, buds, and foliage of the plant in full color; the colors shown are as true as can be reasonably obtained by conventional photographic procedures. The photographs are of whole plants about 3 months old, grown in a field in Gilroy, Calif. in mid July 2005.

DESCRIPTION OF THE NEW CULTIVAR

Figure 1:
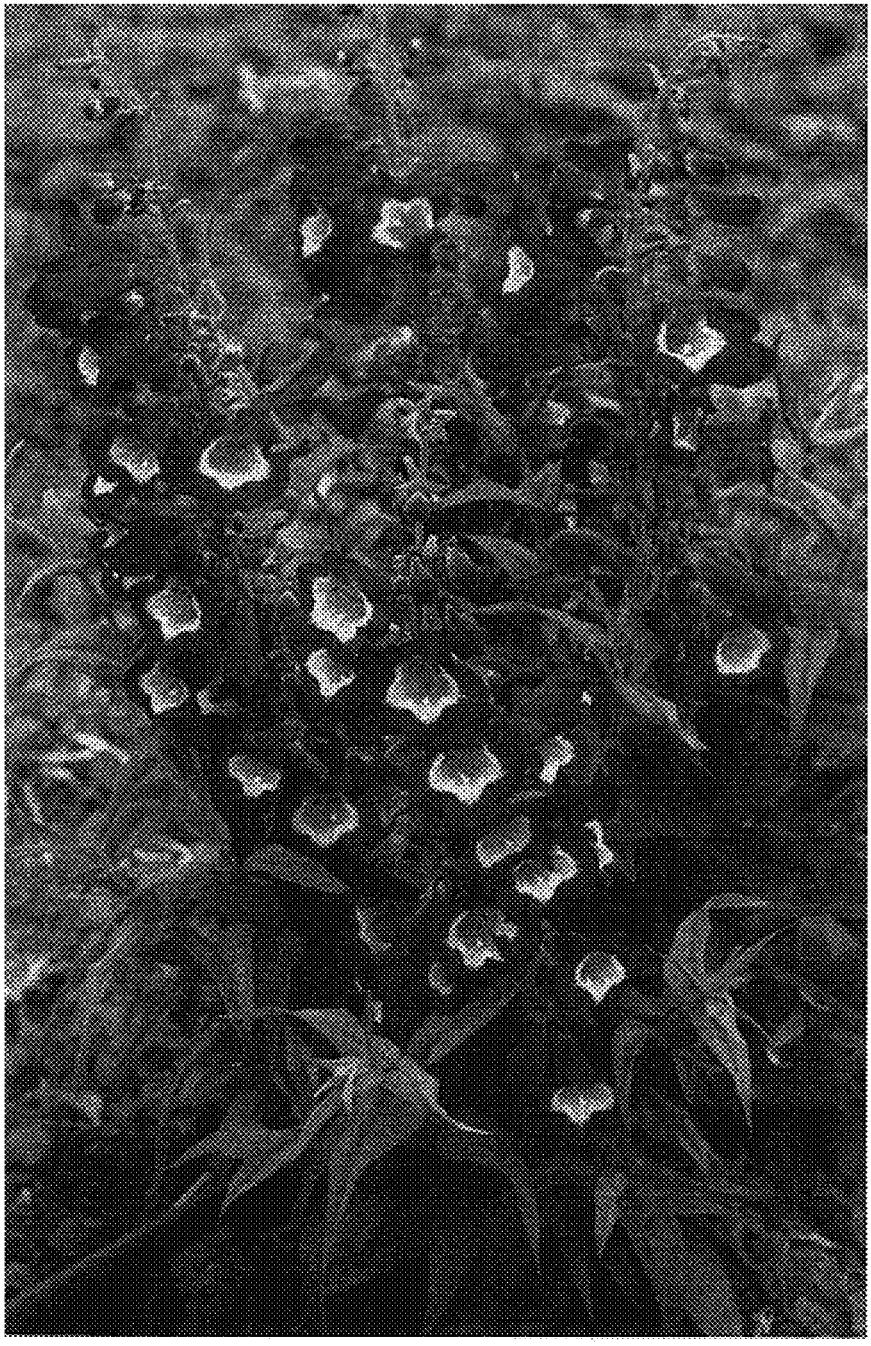
FIG. 1 shows the overall plant habit, including blooms, buds, mature foliage, and plant habit.
Figure 2:
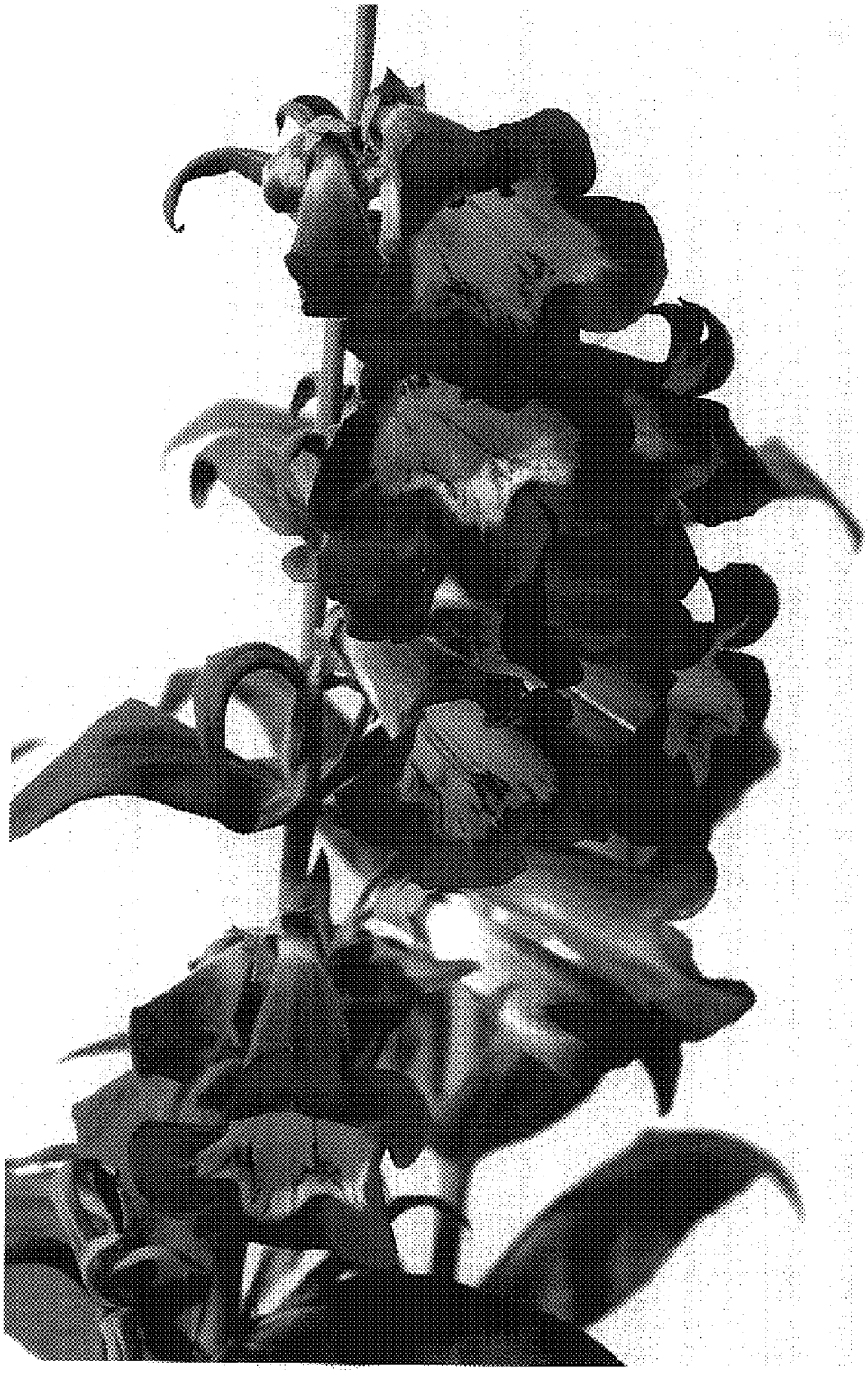
FIG. 2 shows a close-up of the mature inflorescences.

The following detailed descriptions set forth the distinctive characteristics of 'Pheni Magna'. The data which define these characteristics were collected from asexual reproductions carried out in Gilroy, Calif. The plant history was taken on nine to eleven-week-old plants grown in Hillscheid, Germany in 2005. Rooted cuttings were planted into 12-cm plastic pots placed in a greenhouse. The plants were not pinched, so they mostly developed into single-stem plant habits. Most observations were made after nine to ten weeks at the beginning of flowering. Color readings were taken under natural light. Color references are primarily to the R.H.S. Colour Chart of The Royal Horticultural Society of London (R.H.S.) (2001 edition).

DETAILED BOTANICAL DESCRIPTION OF THE NEW PLANT

Classification:

*Family.*—Scrophulariaceae.

*Botanical name.*—*Penstemon hartwegii* Benth.

Parentage:

*Female parent.*—'110-1' a proprietary red-flowered *Penstemon* plant (unpatented).

*Male parent.*—'112-1' a proprietary lavender-flowered *Penstemon* plant (unpatented).

Growth:

*Form.*—Herbaceous perennial; suffrutescent; tolerates only slight frost and because of its short cultivation time, it is usually cultivated as an annual plant.

*Habit.*—Un-pinched plants develop one flowering main stem and only occasionally, weaker secondary branches at the base; for commercial purposes, the young plants are usually pinched so that 5–10 stems of equal size will develop.

*Height.*—71 cm for a 9-week-old single-stem plant (as measured from the soil to the tip, including the inflorescence).

*Width.*—Up to 20 cm.

*Time to produce a finished flowering plant.*—About 10–11 weeks for as a single-stem plant in a 5-inch pot; 13 weeks for a branched plant planted outdoors.

*Outdoors plant performance.*—Use in garden beds or in container planting.

*Time to initiate and develop roots.*—21 days.

*Root description.*—Somewhat fleshy at the base, mainly fibrous, and self-branching.

Leaves:

*Arrangement.*—Opposite and decussate.

*Shape.*—Lanceolate.

*Apex.*—Acute to acuminate.

*Base.*—Sessile.

*Margin.*—Very shallowly crenate with short bristles.

*Immature.*—Color:—Upper surface: RHS 143B. Lower surface: RHS 138B. Texture: Smooth with very fine pubescence.

*Mature* (*fully expanded*).—Length: 14.0 cm. Width: 4.0 cm. Color: General: Grass green. Upper surface: RHS 143A. Lower surface: Between RHS 138A and RHS 138B. Texture: Smooth, glabrous, and slightly glossy.

*Venation.*—Type: Pinnate; with the midrib of the lower side protruding; other veins are hardly visible. Color (midrib, lower side): RHS 145B (pale green).

Stems:

*Length.*—48 cm as measured from the base, excluding the inflorescence.

*Diameter.*—0.7 cm as measured at the midpoint.

*Internode length.*—3–4 cm.

*Color.*—RHS 143D (light green).

*Texture.*—Appears smooth, with sparse pubescence.

*Anthocyanin.*—RHS 184A (purple-brown) may occur in places.

Flower bud:

*Shape.*—Tube-shaped with a closed end.

*Diameter.*—1.5 cm.

*Length.*—4.0 cm.

*Color* (*at tight bud*).—RHS 71C at the tip with RHS 69C (pale pink) on the funnel-shaped part.

Inflorescence:

*Inflorescence type.*—Terminal (appears almost as a raceme), but rather thyrse.

*Blooming habit.*—Intermittent; removing of spent inflorescences enhances new flowering.

*Quantity of inflorescence per plant.*—One (for a single stem, un-pinched plant).

*Lastingness of individual blooms on the plant.*—5–6 days.

*Fragrance.*—None.

*Inflorescence length.*—Approximately 30 cm.

*Inflorescence width.*—Up to 13 cm.

*Penduncle.*—Color: RHS 145A (light green). Length: 3–5 cm. Diameter: 0.2–0.3 cm. Texture: Pubescent (density covered with short hair).

Flower:

*Type.*—Zygomorphic; funnel-shaped, 5-lobed, main part of petals fused; petal lobes are free and directed outward.

*Floret quantity* (*per raceme*).—About 20–25.

*Shape.*—Funnel-shaped.

*Floret diameter.*—4.2 cm.

*Floret depth.*—4.5 cm.

*Color.*—General: Red-purple/magenta with white. Petal lobes: RHS 67A. Corolla (outer color): Upper side is RHS 67B, fading towards lower side to RHS 75D. Corolla (inside color): RHS 69D (white to palest pink) with weak RHS 67A (purple) markings.

*Petals* (*lobes*).—Quantity: 5. Arrangement: Two upper lobes with two lateral lobes and one lower lobe. Apex: Rounded to obtuse. Base: Fused and funnel-shaped. Margin: Entire. Texture: Smooth.

*Upper lobes, size.*—Length (from the Corolla opening): 1.3 cm. Width: 1.3 cm.

*Lateral lobes, size.*—Length (from the Corolla opening): 1.3 cm. Width: 1.5 cm.

*Lower lobe.*—Length (from the Corolla opening): 1.4 cm. Width: 1.6 cm.

*Sepals.*—Quantity: 5. Color: RHS 143C. Length: 0.8-0.9 cm. Width: 0.7 cm. Shape: Ovate. Apex: Acute. Base: Attenuate. Anthocyanin: RHS N77B (weak purple) which may occur at the lateral margins. Texture: Rough and pubescent.

*Pedicels.*—Color: RHS 143C (light green). Length: 0.6 cm. Diameter: 0.1 cm. Texture: Pubescent.

Reproductive organs:

*Stamens.*—Quantity: 5 total, of which 4 are fertile. Filament: Color: RHS 155D (white). Length: 2.9–3.2 cm. Diameter: 0.1 cm. Anther color: RHS N186A (nearly black). Pollen amount: Abundant. Pollen color: RHS 4D (pale-yellow).

*Pistils.*—Quantity: 1. Length: 3.3 cm. Stigma color: RHS 155A (white). Style color: RHS 73A (pink) and upper part is RHS 155D (white).

Fruit and seed set: Plants are fertile; frequently, ovary is ovate, 0.6 cm in length and 0.4 cm in diameter; when the corolla drops, the ovary develops into a seed capsule (ovate in shape) of about 1.1 cm in length and 0.7 cm in diameter.

*Seed.*—Color: RHS 200A. Shape: Irregularly round (a few more oblong), wrinkled and pitted. Diameter: 0.15 cm.

Disease and insect resistance: Has not been observed.

COMPARISON WITH PARENTAL AND COMMERCIAL CULTIVARS

'Pheni Magna' differs from the female parent, proprietary *Penstemon* plant, '110-1' (unpatented), in that 'Pheni Magna' has red-purple flowers, while '110-1' has red flowers. Additionally, 'Pheni Magna' has darker green foliage and stronger branching than '110-1'.

'Pheni Magna' differs from the male parent, proprietary *Penstemon* plant '112-1' (unpatented), in that 'Pheni Magna' has red-purple flowers, while '112-1' has lavender flowers. Additionally, 'Pheni Magna' has a more compact and better branching plant habit than '112-1'.

'Pheni Magna' differs from the commercial cultivar 'Cathedral Hot Rose' (patent status unknown) in that 'Pheni Magna' develops more branches and is generally more compact than 'Cathedral Hot Rose'. Additionally, 'Pheni Magna' flowers earlier than 'Cathedral Hot Rose'.

I claim:

1. A new and distinct cultivar of *Penstemon* plant as shown and described herein.

* * * * *